United States Patent [19]

Lancia et al.

[11] Patent Number: 5,698,713
[45] Date of Patent: Dec. 16, 1997

[54] PROCESS FOR THE PRODUCTION OF GAMMA-BUTYROLACTONE

[75] Inventors: Rosa Lancia, Scanzorosciate; Angelo Vaccari, Bologna; Carlo Fumagalli, Alessandro, all of Italy; Erich Armbruster, Naters, Switzerland

[73] Assignee: Lonza S.P.A., Milan, Italy

[21] Appl. No.: 696,871

[22] PCT Filed: Feb. 17, 1995

[86] PCT No.: PCT/EP95/00589

§ 371 Date: Feb. 20, 1997

§ 102(e) Date: Feb. 20, 1997

[87] PCT Pub. No.: WO95/22539

PCT Pub. Date: Aug. 24, 1995

[30] Foreign Application Priority Data

Feb. 22, 1994 [IT] Italy .................................. MI94A0317

[51] Int. Cl.$^6$ .................................................. C07D 307/26
[52] U.S. Cl. .................................................. 549/325
[58] Field of Search .................................................. 549/325

[56] References Cited

U.S. PATENT DOCUMENTS

| | | | |
|---|---|---|---|
| 3,065,243 | 11/1962 | Dunlop et al. | 260/343.6 |
| 3,580,930 | 5/1971 | Miya et al. | 260/343.6 |
| 4,001,282 | 1/1977 | Miller | 260/343.6 |
| 4,105,674 | 8/1978 | De Thomas et al. | 260/343.6 |
| 4,965,378 | 10/1990 | Budge et al. | 549/508 |
| 5,072,009 | 12/1991 | Budge et al. | 549/508 |
| 5,347,021 | 9/1994 | Taylor et al. | 549/325 |

FOREIGN PATENT DOCUMENTS

| | | |
|---|---|---|
| 0332140 | 6/1989 | European Pat. Off. . |
| 1768191 | 4/1970 | Germany . |
| 1168220 | 10/1969 | United Kingdom . |
| WO 86.03189 | 6/1986 | WIPO . |
| WO 86/07358 | 12/1986 | WIPO . |
| WO 91/16132 | 10/1991 | WIPO . |

OTHER PUBLICATIONS

*Chemical Abstracts*, vol. 117, No. 15 (1992), 150868n (English translation).

Primary Examiner—Amelia A. Owens
Attorney, Agent, or Firm—Fisher, Christen & Sabol

[57] ABSTRACT

Disclosed is a process for the production of gamma-butyrolactone from maleic anhydride or succinic anhydride by hydrogenation in the presence of a catalyst composition comprising the mixed oxides of copper, zinc and zirconium.

13 Claims, No Drawings

PROCESS FOR THE PRODUCTION OF GAMMA-BUTYROLACTONE

This application is a 371 of PCT/EP95/00589 filed Feb. 17, 1995.

The present invention relates to a process for vapour phase catalytic hydrogenation of maleic anhydride to gamma-butyrolactone using a three-component catalyst composition comprising copper-, zinc- and zirconium oxides. Gamma-butyrolactone (GBL) became industrially available in the 1940's as a result of the work of W. Reppe. The Reppe process starts from acetylene and formaldehyde to yield 1,4-butanediol (BDO), which is dehydrogenated to GBL. The main use of GBL is as an intermediate for pyrrolidone, N-methylpyrrolidone, N-vinylpyrrolidone, herbicides, pharmaceuticals and rubber additives. In smaller amounts it is used as a solvent mainly in the polymers field. After maleic anhydride (MA) price has lowered, due to new industrial processes that use butane as a feedstock instead of benzene, fluidized bed and non-aqueous product recovery, this molecule is regarded as a building block for several derivatives. Hydrogenation of MA or its esters to GBL, tetrahydrofuran (THF) and BDO has been widely studied. Liquid phase hydrogenation of MA to GBL has been employed in commercial production, but never got great industrial importance. Vapour phase catalytic hydrogenation of MA or its esters to GBL has been disclosed in many patents, but did not reach industrial realisation. The only process that met industrial practice is diethylmaleate hydrogenation to produce BDO as disclosed in WO 86/03189. A similar process was disclosed for GBL production in WO 86/07358 but from the economical point of view direct hydrogenation of MA to derivatives must be preferred. Dunlop in U.S. Pat. No. 3,065,243 disclosed a process for hydrogenation of maleic or succinic anhydride or their esters to GBL in the vapour phase, using copper chromite as a catalyst but conversion and selectivity, were not satisfactory. Similar results were obtained using a copper-zinc oxide catalyst, as disclosed in British patent 1 168 220. Miller in U.S. Pat. No. 4,001,282 suggested the addition of water to improve catalyst life by reducing tar formation, but did nor mention improvements in conversion or selectivity. Noble metal based catalysts such as Cu/Pd and Cu/Pt were disclosed by De Thomas in U.S. Pat. No. 4,105,674.

Cu/Zn/Cr catalysts were described by Miya in U.S. Pat. No. 3,580,930 and Cu/Zn/Cr/Al catalysts by Attig in EP 332 140. None of these processes have reached industrial application, probably because of not completely satisfactory results in terms of GBL yield, productivity or byproducts. Moreover it has to be pointed out that chromium containing catalysts should be avoided for environmental reasons. Recently a process has been disclosed by Taylor in WO 91/16132, concerning MA vapour phase hydrogenation over a Cu/Zn/Al catalyst activated at 400°–525° C. Process conditions are also described to achieve commercial operation, but the need of high temperature activation is a disadvantage in terms of plant design and operation. The object of the invention is to provide a process for the production of gamma-butyrolactone from maleic anhydride or succinic anhydride which exhibits a very high selectivity at an essentially quantitative conversion of the starting material without requiring noble metals or toxic compounds. A further object of the invention is to provide a catalyst for this process which is easy to prepare and maintains its activity even after prolonged operation.

The present invention provides a process for the hydrogenation of maleic or succinic anhydride to GBL over a Cu/Zn/Zr catalyst. The Cu/Zn/Zr catalyst comprises a catalytically active oxide material and optionally an essentially inert support. The catalytically active oxide material comprises a mixed oxide of copper, zinc and zirconium, the metals content of which is composed of 10–40 wt % of copper, 10–40 wt % of zinc, and 30–70 wt % of zirconium. Preferably the composition comprises 20–30 wt % of copper, 20–30 wt % of zinc and 40–60 wt % of zirconium. In the active state, the catalytically active oxide material may include some metallic components (e.g. metallic copper) formed in the activation step or during the hydrogenation. The catalyst composition is therefore given in the form of an elemental weight ratio, which is not affected by variations of oxidation numbers.

The catalyst can be prepared by coprecipitating a catalyst precursor from a mixed solution of water-soluble salts of copper, zinc and zirconium. Preferably the mixed solution is prepared by mixing an aqueous solution containing water-soluble salts of copper and zinc with an aqueous solution of a water-soluble zirconium salt. The coprecipitation is suitably accomplished by adding a solution of sodium hydroxide, sodium carbonate, ammonia, ammonium carbonate, or another suitable alkaline compound under stirring. Examples of the water-soluble salts of copper, zinc and zirconium used as starting materials include halides, nitrates and acetates. Preferably the corresponding chlorides (i.e., cupric chloride, zinc chloride and zirconium oxychloride) are used as starting materials. The coprecipitated catalyst precursor is recovered by filtration, washed thoroughly, and dried, typically at about 100° C.

After drying, the catalyst precursor is calcined preferably in air, at a temperature of 300°–500° C. Typically, the calcination temperature is about 380° C.

During calcination copper, zinc and zirconium mixed oxides are formed and an essentially or at least partially amorphous state is maintained.

The thus obtained mixed oxide is subjected to an activation treatment comprising gradually increasing its temperature to about 350° C. in the presence of a hydrogen-containing gas. For example, the hydrogen-containing gas in the activation treatment may be a mixture of hydrogen and nitrogen. After the activation treatment the catalyst is ready for use. Activation requires a time varying from 10 h to several days, depending on reactor size and design. Since catalyst reduction is an exothermic reaction, if a reactor does not provide an efficient heat removal the hydrogen-containing gas must be suitably diluted or the space velocity must be increased to control exothermic peaks. Hydrogen dilution results in longer time in the exothermic phase of activation. Large adiabatic reactors usually require the longest activation times. A vaporous mixture of a hydrogen containing gas and maleic anhydride or succinic anhydride or a mixture thereof is fed into a reactor packed with the above described catalyst. Optionally, the catalyst, can be supported by an essentially inert support material. Suitable examples of essentially inert support materials include silica, alumina, silica-alumina compounds (e.g. mullite), silicon carbide, steatite, titania and zirconia.

The molar ratio of hydrogen to anhydride in the feed is preferably between 50 to 1 and 500 to 1 and more preferably between 80 to 1 and 250 to 1. Low $H_2$ to anhydride ratios result in tar formation and short catalyst life. The reaction temperature is preferably between about 200° and 300° C., and more preferably between about 230° and 280° C. The reaction pressure is preferably between about atmospheric and 80 bar, more preferably at about 1 to 20 bar.

The vaporous mixture which is fed into the reactor can be prepared by vaporising the molten anhydride(s) in a stream of hot hydrogen gas. It is also possible to use a solution of the anhydride(s) in a suitable solvent. Advantageously, gamma-butyrolactone is used to dissolve the anhydrides. As it is known by those skilled in the art, temperature and pressure range in the hydrogenation reaction depend on the desired product mixture. Increasing temperature will result in the mix containing more THF, while increasing pressure will yield substantial amounts of BDO.

The following examples illustrate this invention in more detail.

EXAMPLE 1

Copper chloride dihydrate, zinc chloride and zirconium oxichloride were dissolved in water to give a mixed solution having a metal weight ratio of Cu:Zn:Zr of 25:25:50. A NaOH solution was added under stirring; one mole of NaOH was used per mole of Cl in the metalchlorides solution, plus a slight excess. The slurry was filtered in a filter press and the filter cake directly washed in the filtration apparatus and then dried in an oven for 12 hours at 100° C. The catalyst was calcined in air at 380° C. for 24 hours.

EXAMPLE 2

The catalyst preparation of example 1 was repeated using a solution with a metal weight ratio of Cu:Zn:Zr of 30:30:40.

EXAMPLE 3

The catalyst preparation of example 1 was repeated using a solution with a metal weight ratio of Cu:Zn:Zr=35:35:30.

EXAMPLE 4

The catalyst preparation of example 1 was repeated using a solution with a metal weight ratio of Cu:Zn:Zr=20:20:60.

EXAMPLE 5

The catalyst preparation of example 1 was repeated using a calcination temperature of 500° C. for 3 hours.

EXAMPLE 6

A 3 ml microreactor was packed with 2 ml of ground catalyst obtained in example 1. Catalyst activation was carried out employing a 5 vol % hydrogen in nitrogen gas mixture and following the temperature program reported in table I.

TABLE I

| temperature (°C.) | time (h) |
| --- | --- |
| from 25 to 175 | 2 |
| at 175 | 1 |
| from 175 to 225 | 2 |
| at 225 | 1 |
| from 225 to 275 | 2 |
| at 275 | 1 |
| from 275 to 325 | 2 |
| at 325 | 5 |

After catalyst reduction the reactor was fed with a solution of 60 wt % of maleic anhydride (MA) in gamma-butyrolactone (GBL), vaporised by a hot $H_2$ flow (85 ml/min at standard conditions). Yields were determined by on-line gas chromatography.

When 0.08 g/h MA were fed at 245° C. conversion was 100%, GBL molar yield was 98% and THF molar yield 2%.

EXAMPLES 7-19

Example 6 was repeated with different catalysts, feed rates and temperatures. Results are reported in table II.

TABLE II

| Ex. No. | catalyst from ex. | MA feed (g/h) | T (°C.) | GBL yield | SA yield | THF yield | others yield | MA conv. |
| --- | --- | --- | --- | --- | --- | --- | --- | --- |
| 7 | 1 | 0.19 | 245 | 56 | 42 | 2 | — | 100 |
| 8 | 1 | 0.19 | 275 | 97 | 1 | 2 | — | 100 |
| 9 | 2 | 0.08 | 245 | 99 | — | 1 | — | 100 |
| 10 | 2 | 0.19 | 245 | 50 | 40 | — | — | 90 |
| 11 | 2 | 0.19 | 275 | 94 | 5 | 1 | — | 100 |
| 12 | 3 | 0.08 | 245 | 76 | 24 | — | — | 100 |
| 13 | 3 | 0.19 | 245 | 45 | 35 | — | — | 80 |
| 14 | 3 | 0.19 | 275 | 85 | 15 | — | — | 100 |
| 15 | 4 | 0.19 | 275 | 95 | 2 | 2 | — | 99 |
| 16 | 5 | 0.08 | 245 | 56 | 43 | 1 | — | 100 |
| 17 | 5 | 0.08 | 275 | 99 | — | 1 | — | 100 |
| 18 | 5 | 0.19 | 245 | 48 | 13 | 1 | — | 62 |
| 19 | 5 | 0.19 | 275 | 78 | 19 | 1 | 2 | 100 |

THF = tetrahydrofuran
SA = succinic anhydride
others = $C_3$-$C_4$ alcohols and acids
Yields and conversion are expressed in mol %.

We claim:

1. A process for the production of gamma-butyrolactone comprising catalytically hydrogenating maleic and/or succinic anhydride in a vaporous mixture with a hydrogen-containing gas in contact with a catalyst comprising a catalytically active oxide material and optionally an essentially inert support, wherein the catalytically active oxide material comprises a mixed oxide of copper, zinc and zirconium, the metal content of said mixed oxide being composed of 10–40 wt % of copper, 10–40 wt % of zinc and 30–70 wt % of zirconium.

2. A process according to claim 1 wherein the metal content of the mixed oxide of copper, zinc and zirconium is composed of 20–30 wt % copper, 20–30 wt % of zinc, and 40–60 wt % of zirconium.

3. A process according to claim 2 wherein the catalytically active oxide material is prepared by coprecipitating a catalyst precursor from a mixed solution of water-soluble salts of copper, zinc and zirconium, washing and drying said coprecipitated catalyst precursor, calcining the dried catalyst precursor at 300°–500° C. and activating the thus obtained catalyst in a hydrogen-containing gas under activating conditions which comprise gradually increasing temperature to a final temperature of about 350° C.

4. A process according to claim 3 wherein the water-soluble salts of copper, zinc and zirconium are cupric chloride, zinc chloride and zirconium oxychloride.

5. A process according to claim 4 wherein the catalyst precursor is coprecipitated by adding an aqueous sodium hydroxide solution to the mixed solution of water-soluble salts of copper, zinc and zirconium.

6. A process according to claim 5 wherein the molar ratio of hydrogen to anhydride in the vaporous mixture of the hydrogen-containing gas and the maleic and/or succinic anhydride is between 50 to 1 and 500 to 1.

7. A process according to claim 6 wherein the molar ratio of hydrogen to anhydride is between 80 to 1 and 250 to 1.

8. A process according to claim 7 wherein the hydrogenation is conducted at a temperature of about 200° C. to 300° C.

9. A process according to claim 8 wherein the hydrogenation is conducted at a temperature of about 230° C. to 280° C.

10. A process according to claim 9 wherein the hydrogenation is conducted at a pressure of about atmospheric pressure to 80 bar.

11. A process according to claim 10 wherein the hydrogenation is conducted at a pressure of about 1 bar to 20 bar.

12. A process according to claim 11 wherein the vaporous mixture of the hydrogen-containing gas and the anhydride is prepared by vaporising the anhydride in a stream of hot hydrogen gas.

13. A process according to claim 12 wherein the anhydride before vaporisation is dissolved in gamma-butyrolactone.

* * * * *